US009101289B2

(12) United States Patent
Inoue et al.

(10) Patent No.: US 9,101,289 B2
(45) Date of Patent: Aug. 11, 2015

(54) ULTRASONIC DIAGNOSTIC APPARATUS

(75) Inventors: Shinsuke Inoue, Tokyo (JP); Tetsuya Hayashi, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 371 days.

(21) Appl. No.: 13/809,700

(22) PCT Filed: Jul. 20, 2011

(86) PCT No.: PCT/JP2011/066406
§ 371 (c)(1),
(2), (4) Date: Jan. 11, 2013

(87) PCT Pub. No.: WO2012/014739
PCT Pub. Date: Feb. 2, 2012

(65) Prior Publication Data
US 2013/0114371 A1 May 9, 2013

(30) Foreign Application Priority Data

Jul. 27, 2010 (JP) ................................. 2010-168400

(51) Int. Cl.
*A61B 8/08* (2006.01)
*A61B 8/00* (2006.01)

(52) U.S. Cl.
CPC . *A61B 8/08* (2013.01); *A61B 8/466* (2013.01); *A61B 8/483* (2013.01); *A61B 8/485* (2013.01)

(58) Field of Classification Search
CPC .......... A61B 8/08; A61B 8/466; A61B 8/485; A61B 8/483
USPC .......................................................... 367/11
See application file for complete search history.

(56) References Cited

U.S. PATENT DOCUMENTS

2011/0178404 A1 7/2011 Waki
2013/0114371 A1* 5/2013 Inoue et al. ..................... 367/11

FOREIGN PATENT DOCUMENTS

| EP | 1 684 232 A1 | 7/2006 |
| JP | A-7-178090 | 7/1995 |
| JP | A-7-299060 | 11/1995 |
| JP | A-2000-60853 | 2/2000 |

(Continued)

OTHER PUBLICATIONS

WO2010-026823—translation.*

(Continued)

*Primary Examiner* — Daniel Pihulic
(74) *Attorney, Agent, or Firm* — Oliff PLC

(57) ABSTRACT

An ultrasonic diagnostic apparatus has a storage unit for storing the elastic volume data generated on the basis of the ultrasonic image data obtained by transmitting/receiving ultrasonic waves to/from an object to be examined, an input unit for setting a region of interest in the space which is occupied by the elastic volume data, an extraction unit for extracting from the elastic volume data a voxel group having the voxel values within a set elasticity range which is set based on the elasticity value of the voxels in the region of interest, a 3-dimensional elastic image creation unit for generating a 3-dimensional elastic image basis on the elastic volume data of the voxel group which is extracted by the extraction unit or the elastic volume data excluding the extracted voxel group; and an image display unit for displaying the 3-dimensional elastic image generated by the 3-dimensional elastic image creation unit.

14 Claims, 10 Drawing Sheets

(56) References Cited

FOREIGN PATENT DOCUMENTS

| | | |
|---|---|---|
| JP | 2006218210 A * | 8/2006 |
| JP | A-2008-220802 | 9/2008 |
| JP | A-2008-259605 | 10/2008 |
| JP | 2010148828 A * | 7/2010 |
| WO | WO 2010/020921 A2 | 2/2010 |
| WO | WO 2010/026823 A1 | 3/2010 |

OTHER PUBLICATIONS

JP2008-259605—translation.*
International Search Report issued in International Application No. PCT/JP2011/066406 dated Aug. 30, 2011.
Apr. 25, 2014 Chinese Office Action issued in Chinese Application No. 201180027580.8.

* cited by examiner

ULTRASONIC DIAGNOSTIC APPARATUS

FIELD OF THE INVENTION

The present invention relates to an ultrasonic diagnostic apparatus which displays an ultrasonic image of a diagnostic region in an object to be examined using ultrasonic waves, particularly to a technique that displays an elastic image as a 3-dimensional elastic image showing strain, elasticity modulus, and the like.

DESCRIPTION OF RELATED ART

Besides the ultrasonic diagnostic apparatuses which measure ultrasound reflectance of biological tissue in an object using ultrasonic waves, generate and display reflectance tomographic images of the diagnostic region in which the ultrasound reflectance is converted into luminance, there has been a proposal of an ultrasonic diagnostic apparatus which displays various ultrasonic images for making diagnosis. For example, a type has been proposed which creates tomographic volume data by obtaining plural grayscale tomographic images of the inside of the object at intervals and constructs and displays a 3-dimensional tomographic image based on the plural pieces of grayscale images. By such constructed 3-dimensional images, biological tissue can be observed 3-dimensionally. However, there has been a problem in conventional grayscale 3-dimensional tomographic images such as black and white images that a region of interest cannot be seen or is difficult to see at the time of image construction by volume rendering when, for example there is volume data of another region in front of the line of sight.

Given this factor, a method has been proposed which displays, for example an image of a blood vessel specified by volume rendering as spectrum by specifying the blood vessel in a 3-dimensional tomographic image (for example, Patent Document 1). Also, a technique has been proposed which acquires the average value of the voxel values in a region of interest which is set in tomographic volume data and sequentially extracts the adjacent voxels of which the voxel value is within a set range as the same region on the basis of the upper-limit value or lower-limit value of the set voxel value, so as to display a 3-dimensional image related to the volume (block) of a desired region (for example, Patent Document 2).

On the other hand, there has been a method which measures the strain by obtaining the correlation of a pair of grayscale tomographic data sets of which the same portions are imaged and performing spatial differentiation on the moving distance, for example the displacement of biological tissue, or measures the elasticity modulus by giving change of pressure to the biological tissue as tissue diagnosis, so as to generate and display an elasticity image of the strain or elasticity modulus. For generating and displaying elastic images, red, blue or other hue information is given thereto mainly on hard regions in biological tissue in accordance with the strain or elasticity modulus of the biological tissue, for facilitating diagnosis of the extent or size of tumors (for example, Patent Document 3). An elastic image is appended with red, blue or other hue information on mainly hard regions in biological tissue in accordance with the strain or elasticity modulus of the biological tissue, for facilitating diagnosis of the extent or size of tumors (for example, Patent Document 3). Also, a technique has been proposed which acquires the elasticity value such as the strain, elasticity modulus, etc. in spatially consecutive positions and creating the elastic volume data in the same manner as 3-dimensional grayscale images, for constructing and displaying 3-dimensional elastic images on the basis of the created volume data.

PRIOR ART DOCUMENTS

Patent Documents

Patent Document 1: JP-H07-178090
Patent Document 2: JP-H07-299060
Patent Document 3: JP-2000-60853

Technical Problems

Elastic images are originally for facilitating recognition of hard regions such as tumors, thus 3-dimensional elastic images are also for capturing the position or extensity of blocks in hard regions such as tumors. However, tissues such as tumors are generally enfolded by surrounding soft tissues in 3-dimensional elastic images, thus hard regions are hidden by soft regions which makes them difficult to be recognized. Also, superficial portions are often hardened due to pressure for deforming tissues of an object, thus regions other than desired diagnostic regions are often displayed as being hard as well, which makes it difficult to easily recognize the hardness in desired target regions.

The objective of the present invention is to provide the ultrasonic diagnostic apparatus capable of displaying 3-dimensional elastic images showing blocks of biological tissues in which the elasticity values are within a set range.

BRIEF SUMMARY OF THE INVENTION

The ultrasonic diagnostic apparatus of the present invention for achieving the above-described objectives includes:
    a storage unit configured to store the elastic volume data which is generated on the basis of the ultrasonic image data acquired by transmitting/receiving ultrasonic waves to/from an object to be examined;
    an input unit configured to set a region of interest in the space which is occupied by the elastic volume data;
    an extraction unit configured to extract the voxel group having the voxel values within a set elasticity range which is set based on the elasticity value of the voxels in the region of interest;
    a 3-dimensional elastic image creation unit configured to create a 3-dimensional elastic image by volume rendering the elastic volume data of the voxel group which is extracted by the extraction unit or the elastic volume data excluding the voxel group; and
    an image display unit configured to display the 3-dimensional elastic image generated by the 3-dimensional elastic image creation unit.

Accordingly, in accordance with the present invention, the voxel group which is included in an elasticity range that is set based on the elasticity value of the voxel included in a set region of interest is extracted and a 3-dimensional elastic image is generated based on the elastic volume data of the extracted voxel group, thus the block of the biological tissue having the elasticity which is the same as that in the region of interest can be displayed as a 3-dimensional elastic image. In other words, if the elasticity value of the voxels which are in front in the line of sight are not included in a set elasticity range compared to the block of a desired biological tissue, those voxels are eliminated from the extracted voxel group, whereby facilitating visualization of the displayed 3-dimensional elastic image. In addition, an elasticity range can be set, by acquiring the average value of the elasticity values in the plural voxels included in a region of interest, on the basis of the acquired average value as well as the upper limit value and the lower limit value which will be set separately.

Also, in accordance with the present invention, a 3-dimensional elastic image can be generated by volume rendering the elastic volume data excluding the extracted voxel group. For example, if a region of interest is set on the block of biological tissue which is in front in the line of sight, the voxel group included in the elasticity range which is set on the basis of the block is eliminated. As a result, the biological tissue which is further behind in the line of sight compared to the eliminated voxel group can be displayed on a 3-dimensional elastic image.

In this case, even if the set region of interest is one region, all voxels included in the elasticity range which is set based on the region of interest are extracted from the elastic volume data. In particular, there are times that the voxel group is extracted not only in the block of the biological tissue having the elasticity which is intended by an examiner but also in the block of the biological tissues in the position away from the intended area. As a result, the block of biological tissues can be shown in the 3-dimensional elastic image. Though such 3-dimensional elastic image can be used when there is no influence on making diagnosis, there are cases that only a block of biological tissues in a specific position is desired to be generated and displayed as an image. In such cases, it is preferable to extract the central coordinate in the set region of interest and the voxels consecutively connected to the voxel which is positioned at the central coordinate and set them as a voxel group. In this manner, the only blocks that are connected to the block of biological tissue in the set region of interest will be displayed on a 3-dimensional elastic image, thus the visibility of the 3-dimensional elastic image can be further improved.

Further, in the present invention, it is possible to display on the image display unit a 3-sectioned elastic image in orthogonal three sections on the basis of the command which is input from the input unit, and set a region of interest by the input unit on at least one image of the displayed 3-sectional elastic images. That is, the present invention comprises a cross-sectional image generation unit configured to generate a 3-sectional elastic image of the elastic volume data in the orthogonal three cross-sections set by the input unit and causes the generated image to be displayed on the image display unit, and the input unit inputs and sets the region of interest on the 3-sectional elastic image which is displayed on the image display unit. In this manner, it is possible to visually search a region of interest while a desired orthogonal 3-sectional image is being displayed by operation of the input unit, and input/set, for example a circular mark on the searched region of interest. As a result, the block of biological tissue having a desired elasticity value can be intuitively selected and displayed from among the elastic images of arbitrary cross-sections, which enables reduction of the examiner's work load.

Also, in the present invention, it is preferable that the 3-dimensional elastic image and 3-sectional elastic image are color elastic images in which the hue is converted in accordance with the elasticity value of the pixel. Also, the cross-sectional image generation unit is capable of generating an extracted 3-sectional elastic image in the orthogonal three cross-sections of the elastic volume data in the voxel group which is extracted in the extraction unit or the elastic volume data of the voxel group excluding the extracted voxel group, synthesizing the generated image over the prior 3-sectional elastic image and displaying the synthesized image on the image display unit. In this manner, the elasticity value of the block of desired biological tissue can be observed on the respective synthesized cross-sectional elastic image. Difference of the respective elasticity values, etc. can be observed in detail more easily in a cross-sectional elastic image than observing a block of biological tissues in a 3-dimensional elastic image.

Further, the input unit of the present invention can form a region of interest which is set on the 3-sectional elastic image displayed on the image display unit in a scalable manner. In accordance with the set scale, the extraction unit re-extracts the voxel group for the enlarged or reduced region of interest, and the 3-dimensional elastic image creation unit generates the 3-dimensional elastic image with respect to the re-extracted voxel group. Accordingly, a 3-dimensional elastic image including the region adjacent to a block of desired biological tissues can be generated and displayed, which improves usability of the ultrasonic diagnostic apparatus.

Also, when plural regions of interest are set by the input unit, the extraction unit can extract the voxel group which is included in the respective regions of interest, and the 3-dimensional elastic image creation unit can perform volume rendering on the elastic volume data of the voxel group which is extracted by the extraction unit or the elastic volume data excluding the extracted voxel group, generate the 3-dimensional elastic image and display the image on the image display unit. In this case, the extraction unit can extract the voxels which are positioned at the central coordinate of the respective regions of interest and the voxels that are consecutively connected to the voxel which is positioned at the central coordinate as voxel groups. Also in this case, when volume rendering is performed on the voxel group having the smaller average value of the elasticity values of the voxel in the set two regions of interest, the 3-dimensional elastic image can be generated by setting a small opacity.

Generally in 3-dimensional elastic images, there is a volume edit function which tucks in the edge section of a volume set using the input unit so that the voxel group in the range which is tucked in will not be displayed. By using this function, unnecessary volume sets can be eliminated or cross-sections inside of the volume set can be observed. In the present invention, the volume editing can be performed only on the elastic volume data of the voxel group which is extracted by the extraction unit. It is needless to say that the volume editing can also be performed only on the elasticity volume data excluding the extracted voxel group. In this manner, in such a case that both elastic volume data of the extracted voxel group and elastic volume data excluding the extracted volume data are to be displayed, by performing volume editing on the elastic volume data excluding the extracted voxel group, it is possible to leave the elastic volume data of the extracted voxel group on display and to observe the cross-section of the surrounding elastic volume, which makes it easier to grasp the relationship between the extracted elastic volume data and the surrounding volume data.

Effect of the Invention

In accordance with the present invention, it is possible to display a 3-dimensional elastic image of a block of biological tissue having a set elasticity.

DETAILED DESCRIPTION OF THE INVENTION

Figure 1:
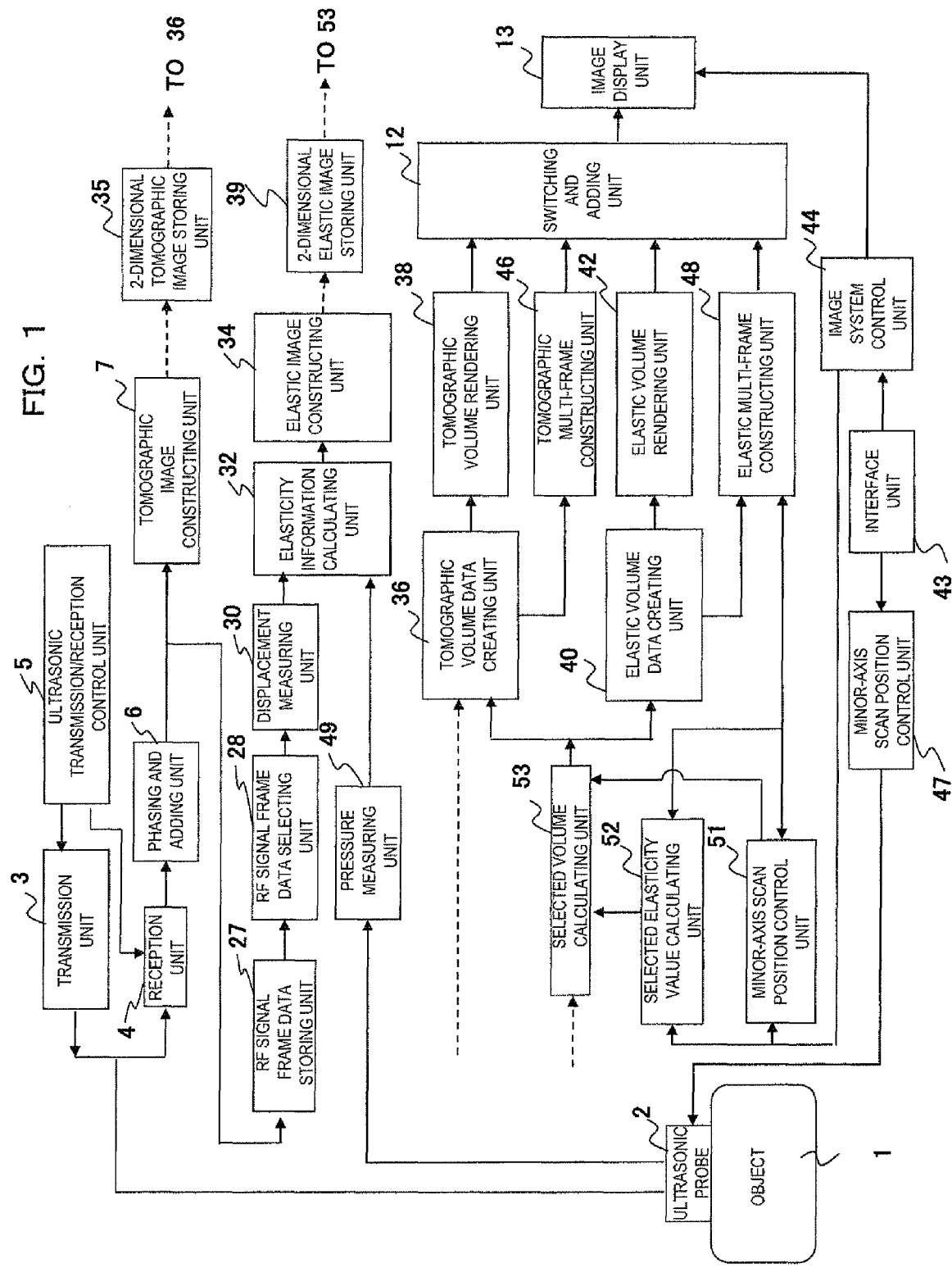
FIG. 1 is a block configuration diagram of the ultrasonic diagnostic apparatus related to the present invention.

FIG. 1 is a block configuration diagram of an embodiment in the ultrasonic diagnostic apparatus related to the present invention, characterized in the method for generating 3-dimensional elastic images. As shown in FIG. 1, the ultrasonic diagnostic apparatus comprises an ultrasonic probe 2 for using by applying to an object 1, a transmission unit 3 configured to repeatedly transmit ultrasonic waves to the object 1 via the ultrasonic probe 2 at intervals; a reception unit 4 configured to receive the time-series reflected echo signals generated from the object 1, a transmission/reception control unit 5 configured to control the switching of transmission and reception of the transmission unit 3 and the reception unit 5, and the phasing and adding unit 6 configured to generate RF signal frame data by phasing and adding the reflected echo signals received in the reception unit 4. A transmission/reception unit is formed by the above-mentioned transmission unit 3, the reception unit 4, the transmission/reception control unit 5 and the phasing and adding unit 6.

The ultrasonic diagnostic apparatus also comprises a tomographic image constructing unit 7 configured to construct a 2-dimensional tomographic image on the basis of the RF signal frame data generated in the phasing and adding unit 6, a 2-dimensional tomographic image storing unit 35 configured to store the 2-dimensional tomographic image constructed by the tomographic image constructing unit 7 together with the acquired position thereof, a tomgoraphic volume data creation unit 36 configured to generate tomographic volume data by performing 3-dimensional coordinate conversion based on the 2-dimensional tomographic image and the acquired position thereof that are stored in the 2-dimensional tomographic image storing unit and generate tomographic volume data, tomographic volume rendering unit 38 configured to construct a 3-dimensional tomgraphic image by performing volume rendering based on the luminance and opacity of the tomographic volume data, a tomographic multi-frame constructing unit 46 configured to create a black and white tomographic image of an arbitrary cross-section from the tomographic volume data created in the tomographic volume data creation unit 36, an elastic image constructing unit 34 configured to construct a 2-dimensional elastic image from the elasticity value of the strain or the elasticity modulus which is calculated in an elasticity information calculation unit 32, 2-dimensional elastic image storing unit 39 configured to store the 2-dimensional elastic image constructed in the elastic image constructing unit 34 and the acquired position thereof, an elastic volume data creation unit 40 configured to perform 3-dimensional coordinate conversion on the basis of the 2-dimensional elastic image and the acquired position thereof stored in the 2-dimensional elastic image storing unit 39 and generate elastic volume data, an elastic volume rendering unit 42 configured to perform volume rendering based on the elasticity value and the opacity of elastic volume data and constructs a 3-dimensional elastic image, an elastic multi-frame constructing unit 48 configured to generate a 2-dimensional elastic image of an arbitrary cross-section from the elastic volume data created in the elastic volume data creation unit 40, a switching and synthesizing unit 12 configured to synthesize a 2-dimensional tomographic image and a 2-dimensional elastic image or 3-dimensional tomographic image and a 3-dimensional elastic image, and an image displayer 13 configured to display images such as a synthetic image which is synthesized by the switching and synthesizing unit 12 and a 2-dimensional tomographic image.

The ultrasonic probe 2 is provided with plural transducers arrayed therein, and has a function to perform electric beam-scanning for transmitting/receiving ultrasonic waves to/from the object 1 via the transducers. Instead, the ultrasonic probe 2 can be provided with plural transducers arrayed in a rectangular shape or a fan shape, capable of 3-dimensionally transmitting/receiving ultrasonic waves by mechanically vibrating the plural transducers in the array-direction thereof and the direction orthogonal thereto. The ultrasonic probe 2 may also be provided with 2-dimensionally arrayed plural transducers to electronically control the transmission and reception of ultrasonic waves. The point is that the ultrasonic probe of the present invention needs to be configured capable of scanning the ultrasonic transmission/reception surface (scan surface) in the minor-axis direction, i.e. the direction orthogonal to the major-axis direction in which plural transducers are arrayed and measuring the reflected echo signals in the volume within a predetermined range of the object 1, so as to measure scan angle θ of the ultrasonic beam in the scan surface and fluctuation angle φ of the ultrasonic beam in the minor-axis direction. The ultrasonic probe 2 is also configured to scan an ultrasonic beam on scan surface by the transmission/reception unit while changing fluctuation angle φ and receive the reflected echo signals from the object 1.

The transmission unit 3 generates transmission pulses for generating ultrasonic waves by activating transducers in the ultrasonic probe 2. The transmission unit 3 has a function to set the convergent point of the ultrasonic waves to be transmitted at a certain depth. Also, the reception unit 4 generates reception RF signals, i.e. reception signals by amplifying the reflected echo signal which is received by the ultrasonic probe 2 at certain gain. The ultrasonic transmission/reception control unit 5 controls components such as the transmission unit 3 and the reception unit 4. The phasing and adding unit 6 performs phase control by inputting the RF signal which is amplified by the reception unit 4, forms an ultrasonic receiving beam for one or more conversion points, and generates RF signal frame data which is tomographic image data.

The tomographic image constructing unit 7 constructs a grayscale image, for example a black and white tomographic image of an object on the basis of the RF signal frame data from the phasing and adding unit 6. In other words, the tomographic image constructing unit 7 performs signal processing such as gain compensation, log compression, detection, edge enhancement or filtering by inputting the RF signal frame data output from the phasing and adding unit 6 based on the setting condition of an image system control unit 44, and generates a 2-dimensional tomographic image. Also, the present invention further comprises an elastic information calculation unit 32 configured to acquire an elasticity value such as the strain or the elasticity modulus from the displacement information measured by a displacement measuring unit 30, and the elastic image constructing unit 34 configured to construct a color elastic image from the elasticity value calculated in the elasticity information calculation unit 32. The color elastic image constructed in the elastic image constructing unit 34 is stored in the 2-dimensional elastic image storing unit 39.

The elastic image data stored in the 2-dimensional elastic image storing unit 39 or the image data generated on the basis of the elastic image data thereof is set to be converted by the switching and synthesizing unit 12 to accord with the display in the image display 13. The present invention is also provided with the image system control unit 44 formed by a CPU which controls the components of the ultrasonic diagnostic apparatus in FIG. 1 and an interface unit 43 which gives commands to the image system control unit 44. An examiner uses the interface unit 43 to variably control color shading, regions of interest (ROI), frame rate and so on of elastic images. Also, a pressure measuring unit 49 measures the pressure to be added to biological tissue of the object 1 at the time of measuring elasticity values. In order to add pressure to biological tissue, commonly known methods can be applied such as the method f pressing and releasing the ultrasonic transmitting/receiving surface of the ultrasonic probe 2 to the object 1, the method of adding dropping impact of a plummet to the object 1 via the ultrasonic probe 2, the method of adding pressure mechanically or using a liquid balloon, the method of adding impulse of ultrasonic pulses with high acoustic pressure, and the method of using body motion such as beats of the object 1 itself. The method for pressure measurement in the pressure measurement unit 49 is to be applied in accordance with the selection of these pressure applying methods.

The RF signal frame data selecting unit 28 selects a pair of RF signal frame data sets from among plural sets of RF signal data from the phasing and adding unit 6 which is stored in the RF signal frame data storing unit 27. For example, the RF signal frame data storing unit 27 sequentially stores in a frame memory the RF signal data that is generated based on the frame rate of the time-series images from the phasing and adding unit 6, and the RF signal frame data selecting unit 28 selects RF signal frame data (N) which is currently stored according to the command from the image system control unit 44 as a first data as well as selecting a set of RF signal frame data (X) from among RF signal frame data group (N−1, N−2, N−3, . . . , N−M) which is stored in the past. Here, N, M and X are index numbers that are given to the sets of RF signal frame data, and are whole numbers.

The displacement measurement unit 30 acquires the displacement, etc. of biological tissue from a pair of RF signal frame data sets. For example, the displacement measuring unit 30 performs 1-dimensional or 2-dimensional correlation process from a pair of RF signal frame data (N) and RF signal frame data (X) that are selected by the RF signal frame data selecting unit 28, and acquires the 1-dimensional or 2-dimensional displacement distribution regarding the displacement or moving vector in the biological tissue corresponding to the respective points in a tomographic image, i.e. the direction and size of the displacement. Here, the block matching method is used for detecting the moving vectors. The block matching method is a process to divide an image into blocks formed by, for example N×N pixels, focuses on a block in a region of interest, searches the block which is most approximated to a focused block from the previous frame, and determines the sample value by the predictive coding, i.e. the difference referring to the searched block.

The data of strain can be calculated by performing spatial differentiation on the moving distance, for example the displacement of biological tissue. Also, the data of elasticity modulus can be calculated by dividing the change of pressure by the change of moving distance. For example, when the displacement measured by the displacement measuring unit 30 is ΔL and the pressure measured by the pressure measuring unit 49 is ΔP, by performing spatial differentiation on ΔL, strain (S) can be obtained by using the equation: S=ΔL/ΔX. Also, Young's modulus $Y_m$ of elasticity data can be calculated by the equation: $Y_m$=(ΔP)/(ΔL/L). The elasticity modulus of the biological tissue which is equivalent to the respective points in a tomographic image can be obtained from this Young's modulus $Y_m$, thus the 2-dimensional elastic image data can be consecutively obtained. The Young's modulus is the ratio of the simple tensile stress which is added to an object with respect to the strain generated in parallel to the tensile force.

The elastic image constructing unit 34 is configured including a frame memory and an image processing unit, configured to store the elastic frame data sequentially output from the elasticity information calculation unit 32 in the frame memory and perform image processing on the stored frame data by the image processing unit. An elastic image is converted into light's three primary colors, i.e. red(R), green (G) and blue (B) on the basis of the elasticity frame data to be displayed as a color image on the image display device 13. For example, the elastic data having a large strain is converted into red color code, and the elastic data having a small strain is converted into blue color code. In addition, the gradation sequence of red(R), green(G) and blue(B) is 256, meaning that 255 is displayed with the maximum luminance and 0 in contrast is displayed with no luminance at all.

Here, the ultrasonic probe 2 is capable of measuring transmitting/receiving directions (θ, φ) at the same time as transmitting/receiving ultrasonic waves, and the tomographic volume data creation unit 36 performs 3-dimensional coordinate conversion on plural 2-dimensional tomographic images on the basis of the transmitting/receiving directions (θ, φ) equivalent to the acquisition positions of the 2-dimensional tomographic images, and creates tomographic volume data. The tomographic volume rendering unit 38 performs volume rendering using the following equations (1)~(3) that construct a 3-dimensional elastic image from the tomographic volume data.

$$Cout(i)=Cout(i-1)+(1-Aout(i-1)) \cdot A(i) \cdot C(i) \cdot S(i) \quad (1)$$

$$Aout(i)=Aout(i-1)+(1-Aout(i-1)) \cdot A(i) \quad (2)$$

$$A(i)=BOpacity[C(i)] \quad (3)$$

C(i) is, when a 3-dimensional tomographic image is viewed from a certain point on a created 2-dimensional projection plane, the luminance of the i-th voxel which exists on the line of sight. Cout(i) is the output pixel value. For example, when the luminance values of N-number of voxels are aligned on the line of sight, luminance value Cout(N−1) in which up to i=0~N−1 are integrated becomes the ultimately output pixel value. Cout(i−1) is the integrated value up to the (i−1)-th voxel.

Also, A(i) is the opacity of the luminance value which exists on the i-th voxel in the line of sight, and is the tomographic opacity table which takes the values of 0~1.0 as shown in the above equation (3). The tomographic opacity table determines the contribution ratio to the output 2-dimensional projection plane (3-dimensional tomographic image) by referring to the opacity from the luminance value.

S(i) is the weighting component for shading which is calculated by the gradient acquired by luminance C(i) and the surrounding pixel values thereof. It shows the accentuation effect, for example by giving 1.0 for the maximum reflection when the light source matches the normal line of the plane which is centered around voxel i and giving 0.0 when the light source and the normal line are orthogonal to each other.

The initial value of both Cout(i) and Aout(i) is 0. As shown in the above equation (2), Aout(i) is integrated each time of passing a voxel and converged into 1.0. Therefore, as shown in the above equation (1), when the integrated value Aout(i−1) of the opacity up to the (i−1)-th voxel is about 1.0, luminance C(i) after the (i−1)-th voxel will not be reflected on the output image.

The tomographic multi-frame constructing unit 46 constructs a cross-sectional tomographic image of the cross-sectional position which is arbitrarily set from the tomographic volume data. The cross-sectional position can be arbitrarily set by an operator using the interface unit 43, and the set cross-sectional position is output to the tomographic multi-frame constructing unit 46 via the image system control unit 44. The cross-sectional position can be set plurally, and the tomographic multi-frame constructing unit 46 outputs plural cross-sectional tomographic images for the plural cross-sectional positions.

The displacement measuring unit 30 measures the displacement of biological tissue from the pair of RF signal frame data which is selected by the RF signal frame data selecting unit 28 from the plural sets of RF signal frame data stored in the RF signal frame data storing unit 27. Then the elasticity information calculation unit 32 calculates the elasticity value on the basis of the measured displacement, and elastic image constructing unit 34 constructs 2-dimensional elastic image data based on the elasticity value acquired from the elasticity information calculation unit 32. Here, any elasticity information of strain, elasticity modulus, displacement, viscosity, strain ratio, etc. can be applied to the elasticity value.

When the ultrasonic probe 2 is capable of 3-dimensional scanning, since RF signal frame data can be spatially and consecutively acquired in the direction orthogonal to the array direction of the plural transducers, elastic images can also be obtained in accordance with the acquired data. The 2-dimensional elastic images that are spatially and consecutively obtained and the acquisition positions thereof are stored in the 2-dimensional elastic image storing unit 39. The elastic volume data creation unit 40 performs 3-dimensional conversion on plural 2-dimensional elastic images on the basis of the transmitting/receiving directions (θ, φ) that are equivalent to the 2-dimensional elastic images stored in the 2-dimensional elastic image storing unit 39 and acquisition positions thereof, and creates the elastic volume data.

The elastic volume rendering unit 42 performs volume rendering on the elastic volume data using the following equations (4)~(6), and generates 3-dimensional elastic images.

$$Eout(i)=Eout(i-1)+(1-Aout(i-1))\cdot A(i)\cdot E(i)\cdot S(i) \quad (4)$$

$$Aout(i)=Aout(i-1)+(1-Aout(i-1))\cdot A(i) \quad (5)$$

$$A(i)=EOpacity[E(i)] \quad (6)$$

Here, E(i) is the elasticity value which exists on the i-th voxel in the line of sight, when a 3-dimensional elastic image is viewed from a certain point on a created 2-dimensional projection plane. Eout(i) is the output pixel value. For example, when the elasticity values of N-number of voxels are aligned on a line of sight, integrated value Eout(N−1) in which elasticity values are integrated up to i=0~N−1 becomes the ultimately output pixel value. Eout(i−1) is the integrated value up to the (i−1)-th voxel. Also, A(i) is the opacity of the elasticity value which exists on the i-th voxel on the line of sight, and the elastic opacity which is set in advance as a table and shown in the equation (6).

S(i) is the weighting component for shading calculated by the gradient which is obtained by elasticity value E(i) and the surrounding elasticity values. It shows the accentuation effect, for example by giving 1.0 for the maximum reflection when the light source matches the normal line of the plane which is centered around voxel i and giving 0.0 when the light source and the normal line are orthogonal to each other.

The initial value of both Eout(i) and Aout(i) is 0. As shown in the above equation (5), Aout(i) is integrated each time of passing a voxel and converged into 1.0. Therefore, as shown in the above equation (4), when the integrated value Aout(i−1) of the opacity up to the (i−1)-th voxel is about 1.0, voxel value E(i) after the i-th voxel will not be reflected on the output image.

The elastic multi-frame constructing unit 48 cuts out the cross-sectional elastic image corresponding to the set cross-section of orthogonal three cross-sections which are input and set by an examiner from the elastic volume data via the interface unit 43, and constructs a cross-sectional elastic image in the set cross-section. The cross-sectional position set from the interface unit 43 is output to the elastic multi-frame constructing unit 48 via the image system control unit 44. The cross-sectional position can be set plurally, and the elastic multi-frame constructing unit 48 outputs plural cross-sectional elastic images for the plural cross-sectional positions.

The switching and synthesizing unit 12 comprises a frame memory, an image processing unit and an image selecting unit. The frame memory is for storing 3-dimensional tomographic images from the tomographic volume rendering unit 38, cross-sectional tomographic images from the tomographic multi-frame constructing unit 46, 3-dimensional elastic images from the elastic volume rendering unit 42 and cross-sectional elastic images from the elastic multi-frame constructing unit 48. Also, the image processing unit adds the 3-dimensional tomographic image and the 3-dimensional elastic image or the cross-sectional tomographic image and the cross-sectional elastic image stored in the frame memory by a set proportion in accordance with the command from the image system control unit 44, and synthesizes the added images. The luminance information and the hue information of the respective pixels in the synthetic images are calculated by adding each set of information in the black and white tomographic image and the color elastic image at a set rate. Further, the image selecting unit selects the 3-dimensional tomographic image and the 3-dimensional elastic image or the cross-sectional tomographic image and the cross-sectional elastic image in the frame memory, and the images to be displayed on the image display unit 13 from among the synthetic image data in the image processing unit, according to the command from the image system control unit 44. In addition, tomographic images and elastic images may also be displayed separately without synthesizing.

The detailed configuration of a selecting coordinate calculation unit 51, a selecting elasticity value calculation unit 52 and a selecting volume calculation unit 53 which are the characteristics of the ultrasonic diagnostic apparatus in the present invention will be described below along with construction procedure of a 3-dimensional elastic image on the basis of the first~seventh embodiments. It is common in all embodiments that cross-sectional elastic images and 3-dimensional elastic images are all constructed as color elastic images, thus color bars of different color tones are displayed in a display area of 3-dimensional elastic images in accordance with the elasticity values. That is, 3-dimensional elastic images and 3-cross-sectional elastic images are color elastic images in which the hues are converted in accordance with the elasticity value of the pixels.

Embodiment 1

Figure 2:
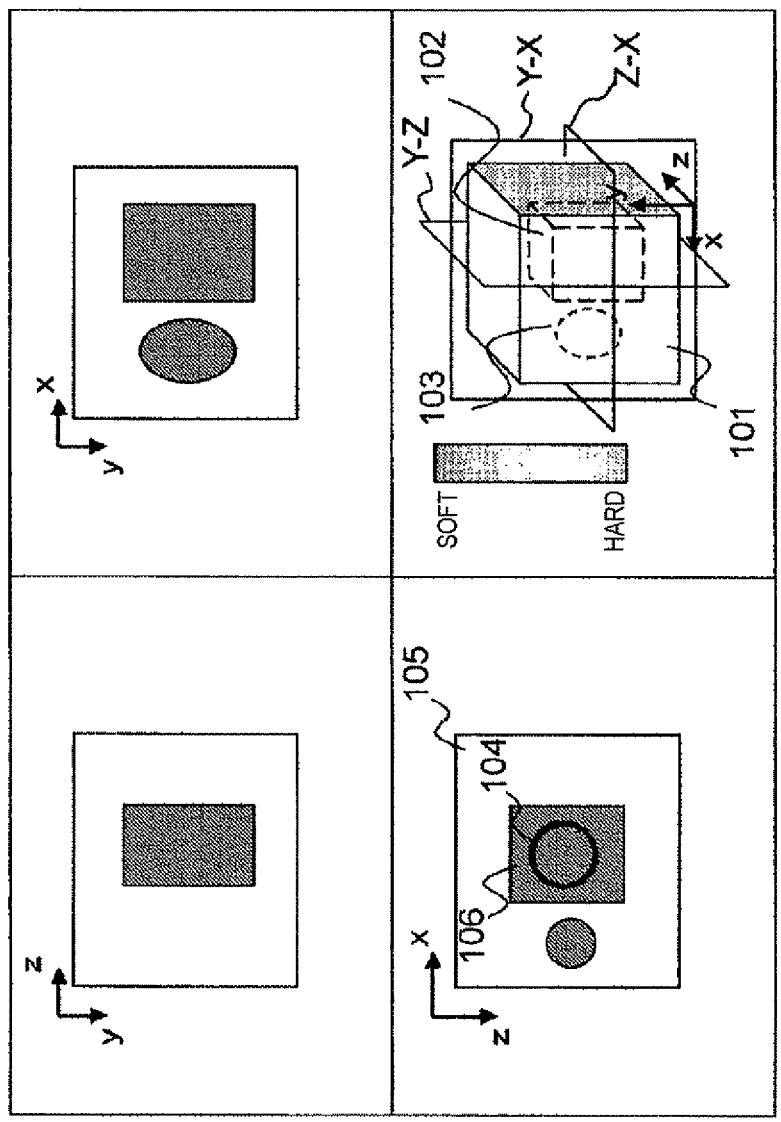
FIG. 2 is a view for explaining an image display example of a first embodiment related to the construction of a 3-dimensional elastic image in the present invention.

FIG. 2 shows an example of a display image in the present embodiment. Images of four planes are displayed in the diagram. The image in the lower-right part in the diagram is a 3-dimensional elastic image, and other images are three cross-sectional elastic images (elastic MPR) in the orthogonal cross-sections (Y-Z, Z-X and Y-X). As shown in the 3-dimensional elastic image, the diagram shows an example of elastic volume data in which a soft volume 101 contains prismatic hard volume 102 and spherical hard volume 103. Here, the volume means a block of biological tissues. Also, the hardness of the prismatic hard volume 102 and the spherical hard volume 103 is assumed to be the same. The elastic volume data is indicated by the XYZ-coordinates of three orthogonal axes. An operator sets a region of interest 104 on an arbitrary elastic MPR image 106 displayed on the image display device 13 via the interface unit 43. Here, an elastic MPR image 105 is displayed by the Z-X plane which vertically intersects with the Y-axis, and the Y-coordinate is expressed by Y=j.

The selecting coordinate calculation unit 51 calculates the central coordinates of, for example the circular region of interest 104 which is set in the interface 43 by the coordinates on the elastic MPR image 105. The central coordinates of the region of interest 104 on the elastic MPR image 105 is set as (Z,X)=(k,i). The selecting coordinate calculation unit 51 calculates central coordinates (X,Y,Z)=(i,j,k) of the region of interest 104 in the elastic volume data from central coordinates (Z,X)=(k,i) and cross-sectional position Y=j in the elastic MPR image 105. Any appropriate method can be used for calculation of the central coordinates in the region of interest 104.

Next, the selecting elasticity value calculation unit 52 outputs the range of elasticity values of the voxels included in the region of interest 104 set by the interface unit 43. For example, when the region of interest 104 is within the coordinate range of (n,l)≤(Z,X)≤(N,L) and the strain value in coordinates (Z,X)=(k,i) is set as s(k,i), average value ms and variance value vs of strain value s can be obtained by the following equations.

$$ms = \frac{1}{(N-n)*(L-l)} \sum_{i=l}^{L} \sum_{k=n}^{N} s(k,i) \quad (7)$$

$$vs = \frac{1}{(N-n)*(L-l)} \sum_{i=l}^{L} \sum_{k=n}^{N} (ms - s(k,i))^2 \quad (8)$$

The selecting elasticity value calculation unit 52 outputs the range from (ms−vs) to (ms+vs) as the set elasticity range.

It is needless to say that the elasticity value other than strain value s may also be used such as the elasticity modulus, displacement, viscosity and strain ratio. A set elasticity range may also be calculated using statistical feature values other than the average value and the variance value of the elasticity value in a region of interest such as the maximum value or the minimum value.

Figure 3:
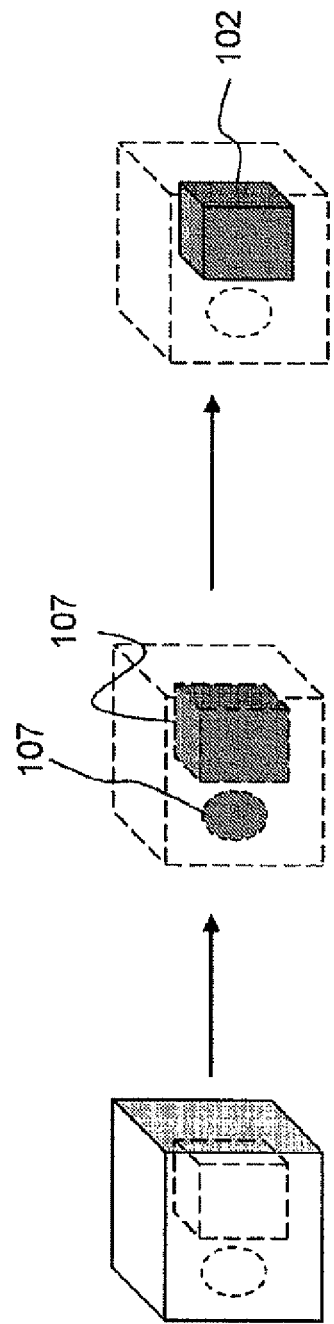
FIG. 3 is a view for explaining an image display example of a process during the first embodiment in the present invention.

As shown in FIG. 3, the selecting volume calculation unit 53 first extracts, from the elastic volume data, elastic volume data 107 having the elasticity value included in the set elasticity range from (ms−vs) to (ms+vs) which is output from the selecting elasticity value calculation unit 52, as voxel groups. Further, from the extracted elastic volume data 107, only the voxel group of the elastic volume data including central coordinate position (i,j,k) output from the selecting coordinate calculation unit 51 is extracted. In the first embodiment, the volume including the central coordinates of the region of interest 104 is a prismatic hard volume 102, thus the prismatic hard volume 102 is extracted as the extracted elastic volume.

The present embodiment is not limited to the above-described example, and the elastic volume data excluding the volume (voxel group) of which the voxel in the set elasticity range being determined by a set region of interest is extracted can be volume rendered for generating and displaying a 3-dimensional elastic image. In this manner, for example, by setting a region of interest in the volume in front in the line of sight which can be an obstacle, the volume which is an obstacle can be eliminated in the 3-dimensional elastic image to be displayed, whereby improving the operation efficiency for the operator.

The present embodiment can be applied not only to 3-dimensional elastic images, but 3-dimensional tomographic images can also be displayed by adapting the coordinates of the volume extracted in the selecting volume calculation unit 53 to the tomographic volume data, extracting and volume rendering only the tomographic volume data corresponding to the extracted elastic volume data.

More specifically, the present embodiment includes a storage unit configured to store the elastic volume data generated on the basis of the ultrasonic image data which is obtained by transmitting/receiving ultrasonic waves to/from an object, an input unit configured to set a region of interest in a space occupied by elastic volume data, an extraction unit configured to extract from the elastic volume data the voxel group having the voxel value within a set elasticity range which is set based on the elasticity value of the voxel in the region of interest, a 3-dimensional elastic image creation unit configured to generate a 3-dimensional elastic image by volume rendering the elastic volume data of the voxel group which is extracted by the extraction unit or the elastic volume data excluding the extracted voxel group, and an image display unit configured to display the 3-dimensional elastic image generated by the 3-dimensional elastic image creation unit.

Also, in accordance with the present embodiment, the extraction unit extracts the central coordinates in a region of interest and the voxels that are consecutively connected to the voxel that is positioned at the central coordinates, as a voxel group.

The present embodiment also comprises a cross-sectional image generation unit configured to generate 3-cross-sectional elastic images of the elastic volume data in three orthogonal cross-sections set by the input unit and cause the generated images to be displayed on the image display unit, and the input unit inputs and sets a region of interest in one of the 3-cross-sectional elastic images displayed on the image display unit.

In accordance with the present embodiment, the cross-sectional image generation unit generates extracted 3-cross-sectinal elastic images in the three orthogonal cross-sections of the elastic volume data of the voxel group which is extracted by the extraction unit or the elastic volume data excluding the extracted voxel group, synthesizes the generated image with the 3-dimensional elastic image, and displays the synthesized image on the image display device.

Embodiment 2

The present second embodiment uses, in the selecting elasticity value calculation unit 52, an input value from outside in the calculation of a set elasticity range. For example, it is an embodiment capable of calculating only the average value of the elasticity values in the region of interest 104 of FIG. 2, and an operator can set using the interface 43 a set elasticity range by inputting upper and lower limit value Ls corresponding to "±vs" of the first embodiment. In this manner, the extent of elasticity values can be freely adjusted by the set elasticity range of ms±Ls, whereby enabling observation of a 3-dimensional elastic image in a region having specified hardness.

Embodiment 3

Figure 4:
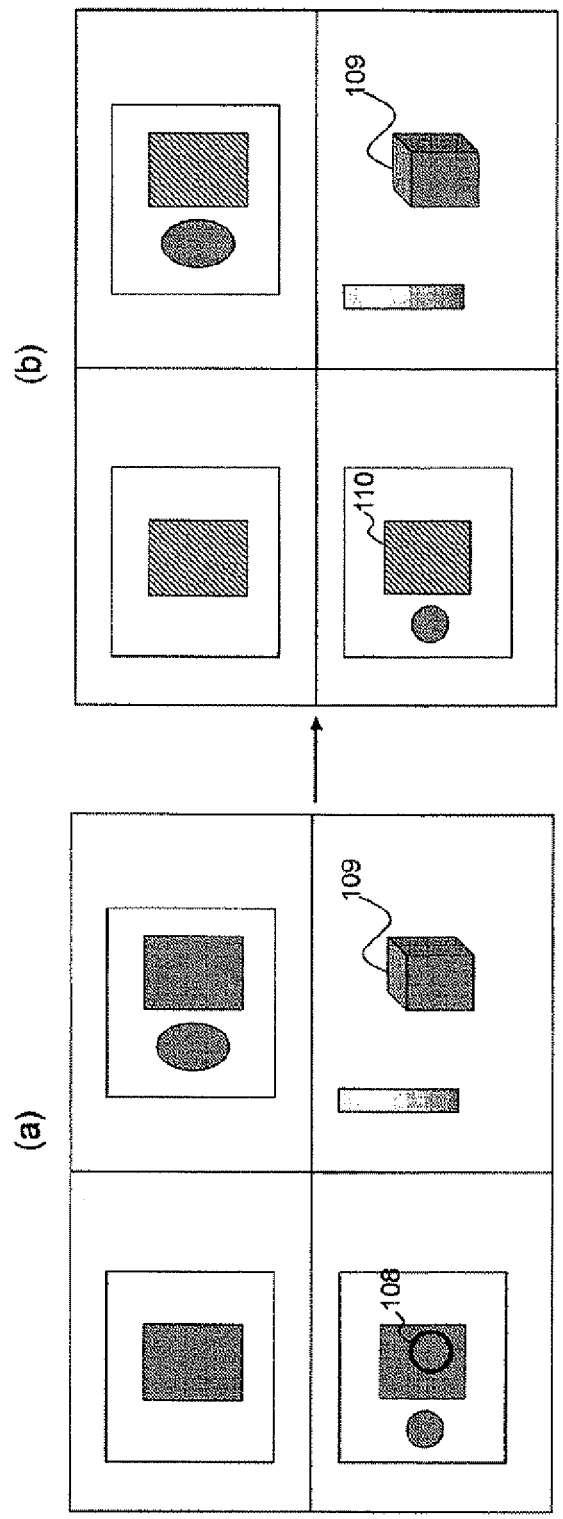
FIG. 4 is a view for explaining an image display example of a third embodiment related to the construction of a 3-dimensional elastic image in the present invention.

FIG. 4 shows an example of a display image in the third embodiment. As shown in the diagram, a region of interest 108 is set by the first embodiment, and an extracted 3-dimensional elastic image 109 is displayed. At this time, the elastic volume creation unit 40 outputs the coordinate information of the extracted volume to the elastic multi-frame constructing unit 48. By doing so, the elastic multi-frame constructing unit 48 outputs a cross-sectional image of the extracted volume as an extracted region 110 in addition to an elastic MPR image of the first embodiment. In response to this, the switching and synthesizing unit 12 superimposes the extracted region 110 over the elastic MPR image 110 of the first embodiment. As for the method of superimposition display, only the contour of the cross-sectional image in the extracted volume can be displayed, or only the extracted volume can be displayed by a different color.

Also, only the extracted region 110 can be displayed by eliminating the elastic MPR image of the first embodiment.

Embodiment 4

Figure 5:
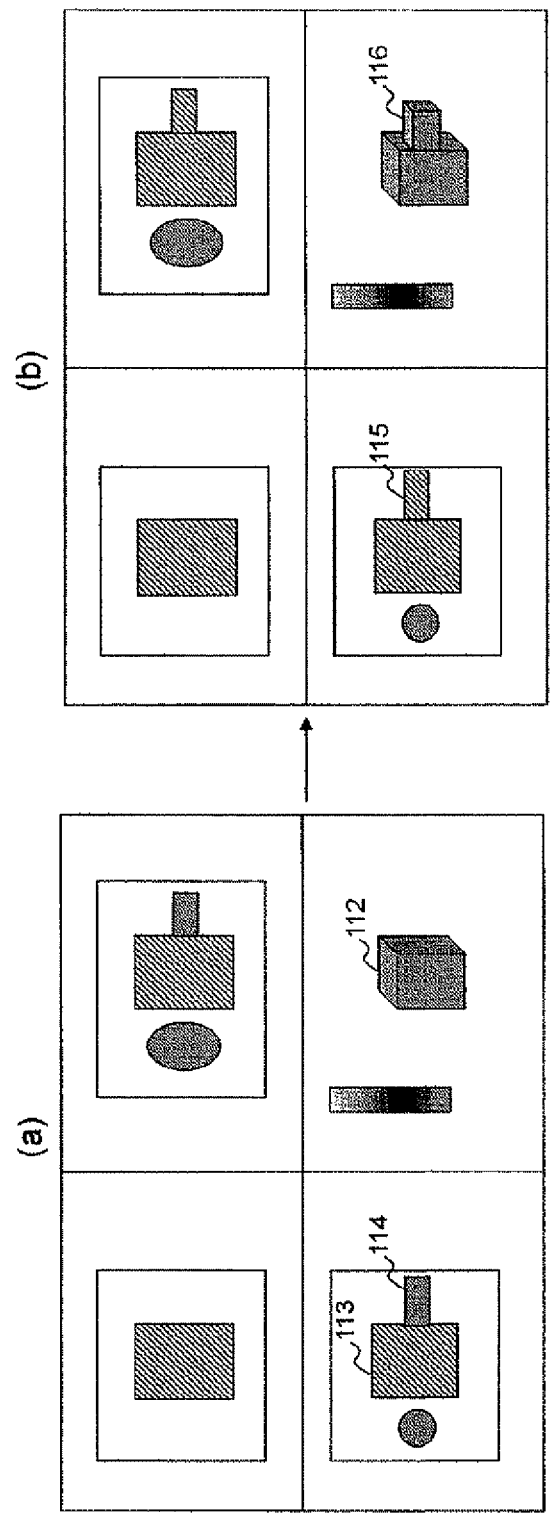
FIG. 5 is a view for explaining an image display example of a fourth embodiment related to the construction of 3-dimensional elastic image in the present invention.

FIG. 5 shows an example of a display image in the fourth embodiment. AS shown in FIG. 4(*a*), as in the first embodiment, an elastic volume 112 is extracted by the set elasticity range that is connected to a set region of interest, and an extracted region 113 is displayed on an elastic MRP image when the third embodiment is applied. However, there are cases that the elastic volume which is equivalent to an image 114 is not displayed on the elastic MPR image, since the elasticity thereof is not included in the set elasticity range of the region of interest.

The present embodiment is capable of handling such cases. The interface unit 43 comprises the function capable of arbitrarily changing the boundary of the extracted region 113. In other words, the operator can operate the interface unit 43 and enlarge the extracted region like an extracted region 115 shown in FIG. 4(*b*). In this manner, the selecting coordinate calculation unit 51 calculates coordinates (i,j,k) (i=l~L, j=m~M, k=n~N) of the enlarged extracted region 115. Then the selecting elasticity value calculation unit 52 calculates the set elasticity range of the enlarged extracted region 114. The selecting volume calculation unit 53 adds the voxels which are adjacent to the voxel having coordinates (i,j,k) (i=l~L, j=m~M, k=n~N) of the enlarged extracted region and included in the extended set elasticity range, and displays an enlarged extracted volume 116. It is needless to say that not only the expansion but also reduction can be performed.

That is, the ultrasonic diagnostic apparatus in the present embodiment is characterized in that the input unit is configured capable of extending or reducing a region of interest set on a 3-cross-sectional elastic image displayed on the image display unit, the extraction unit can re-extract the voxel group with respect to the extended or reduced region of interest, and the 3-dimensional elastic image creation unit can generate a 3-dimensional image for the re-extracted voxel group.

Embodiment 5

Figure 6:
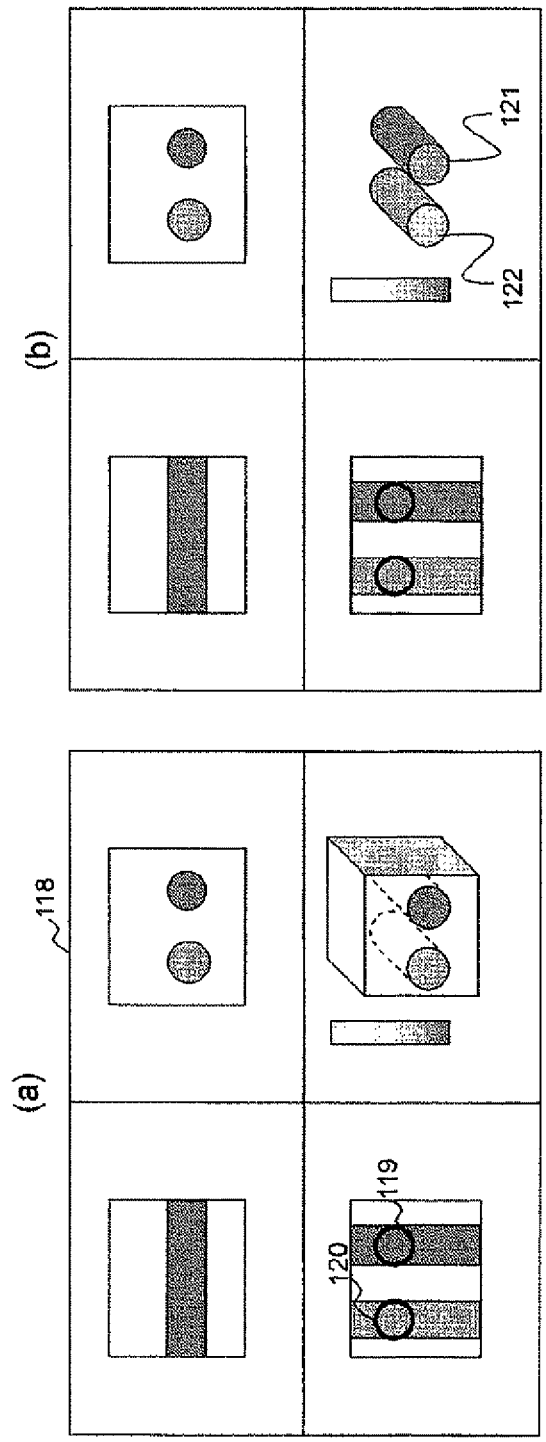
FIG. 6 is a view for explaining an image display example of a fifth embodiment related to the construction of a 3-dimensional elastic image in the present invention.

FIG. 6 shows an example of a displayed image in the present fifth embodiment. FIG. 6(*a*) shows an example that two regions of interest 119 and 120 are set on an elastic MPR image 118 from the interface unit 43. The selecting coordinate calculation unit 51 calculates the respective central coordinates in the region of interest 119 and the region of interest 120. The central coordinates of the region of interest 119 is set as A(i,j,k), and the central coordinates of the region of interest 120 is set as B(s,t,u). The selecting elasticity value calculation unit 52 calculates the set elasticity range respectively for the region of interest 119 and the region of interest 120. The set elasticity range of the region of interest 119 is set as A(s)~A(s'), and the set elasticity range of the region of interest 120 is set as B(s)~B(s'). In this regard, however, A(s)<A(s') and B(s)<B(s').

The selecting volume calculation unit 53 extracts the relevant volume for each of the region of interest 119 and the region of interest 120. In other words, as shown in FIG. 6(*b*), an extracted elastic volume 121 having the elasticity value included in set elasticity value A(s)~A(s') and includes central coordinates A(i,j,k) and an extracted elasticity volume 122 having the elasticity value included in set elasticity range B(s)~B(s') and includes central coordinate position B(s,t,u) are extracted and displayed.

Figure 7:
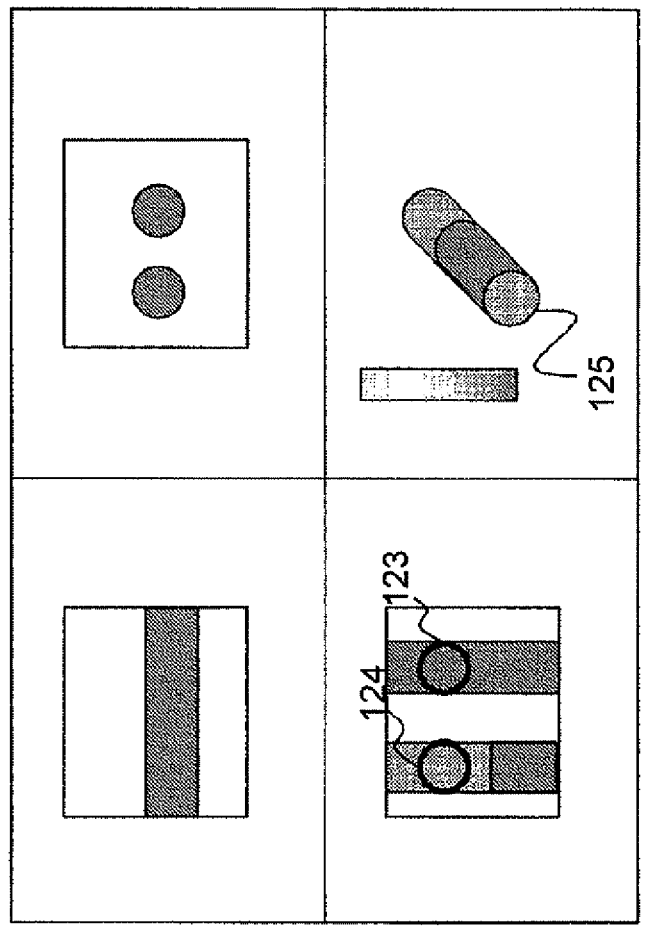
FIG. 7 is a view for explaining an image display example of modification of the fifth embodiment.

In this case, as shown in FIG. 7, only an extracted elastic volume 125 which is included in the set elasticity range of regions of interest 123 and 124 and include the coordinates of the region of interest 124 can be extracted and displayed. Also, while the case in which two regions of interest are set is described in the present embodiment, the cases in which three or more regions of interest are set can also be processed in the same manner.

More specifically, in the present embodiment, when plural regions of interest are set by the input unit, the extraction unit extracts the voxel groups included in the respective regions of interest, and the 3-dimensional elastic image creation unit volume renders the elastic volume data of the voxel group which is extracted by the extraction unit or the elastic volume data excluding the extracted voxel group, and generates a 3-dimensional elastic image to be displayed on the image display unit.

Also in the present embodiment, when plural regions of interests are set by the input unit, the extraction unit obtains the average value of the elasticity values in the plural voxels included in the respective regions of interest and extracts the voxels which are included in the elasticity range having the upper limit value and the lower limit value that are set on the basis of the average value as well as the central coordinates and the voxels which are consecutively connected to the voxel which is positioned at the central coordinates in the respective regions of interest as voxel groups, and the 3-dimensional elastic image creation unit volume renders the elastic volume data of the voxel groups which are extracted by the extraction unit or the elastic volume data excluding the extracted volume groups and generates a 3-dimensional elastic image to be displayed on the image display unit.

Embodiment 6

Figure 8:
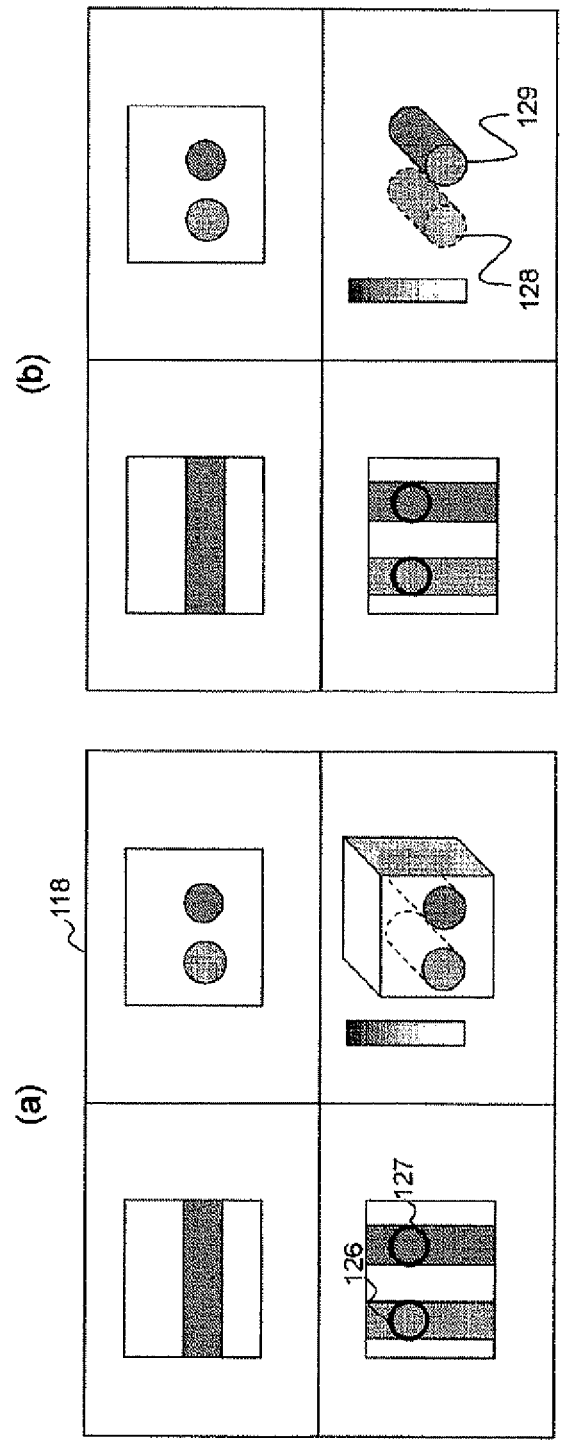
FIG. 8 is a view for explaining an image display example of a sixth embodiment related to the construction of a 3-dimensional elastic image in the present invention.

FIG. 8 shows an example of display images in the sixth embodiment. FIG. 8(a) is an example of the case that two regions of interest 126 and 127 are selected in the interface unit 43. The selecting coordinate calculation unit 51, the selecting elasticity value calculation unit 52 and the selecting volume calculation unit 53 performs calculation as in the fifth embodiment, and extracts extracted elastic volumes 128 and 129. In this case, for example the average value of the elasticity values in the region of interest 126 is set to be smaller than the average value of the elasticity values in the region of interest 127. In this case, at the time that the extracted elastic volume 128 which has the smaller average value of the elasticity values is volume rendered, the elastic volume rendering unit 42 performs rendering by making the opacity of the extracted elastic volume 128 small. In this manner, the volume having the smaller average value of the elasticity values can be displayed more lucidly. In this case, the elasticity modulus, viscosity, etc. can be used as the elasticity value. In addition, in place of the average value of elasticity values, the opacity may also be adjusted using the maximum value of the elasticity value, and so on. Also, the opacity may be made small at the time of rendering the extracted elastic volume having the large average value of the elasticity values. In this case, the strain, the viscosity, etc. can be used as the elasticity value.

Embodiment 7

Figure 9:
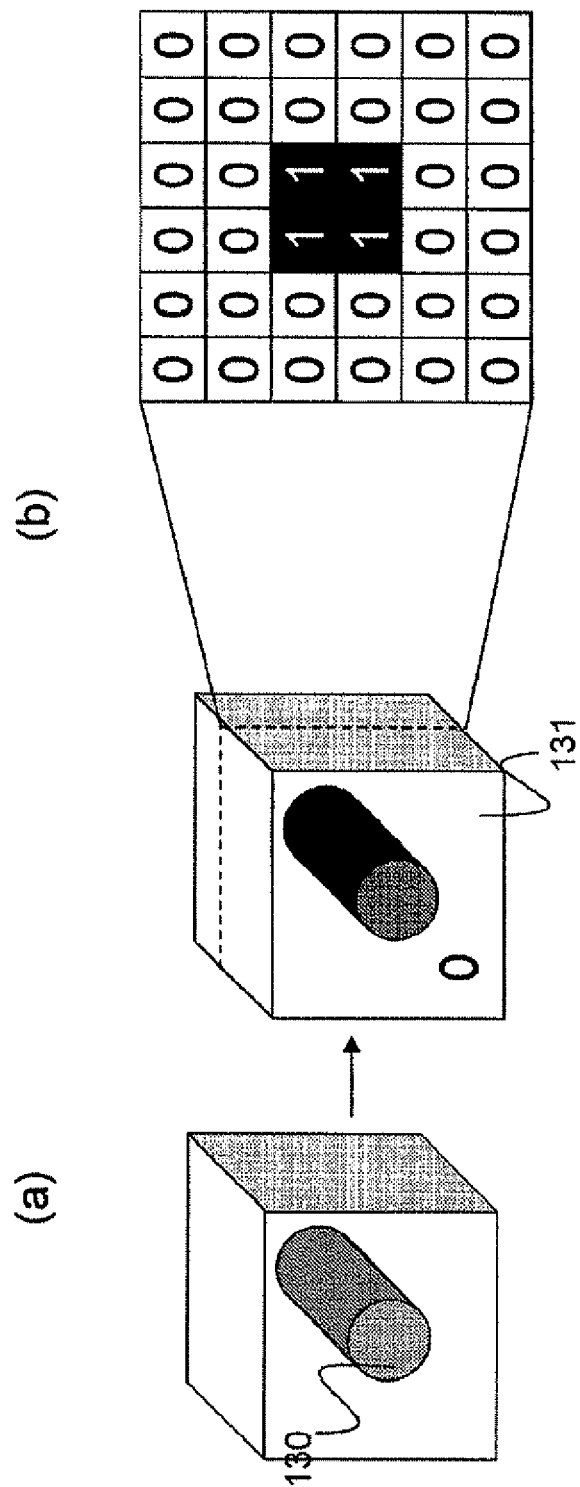
FIG. 9 is a view for explaining the basic principle of a seventh embodiment related to the construction of a 3-dimensional elastic image in the present invention.
Figure 10:
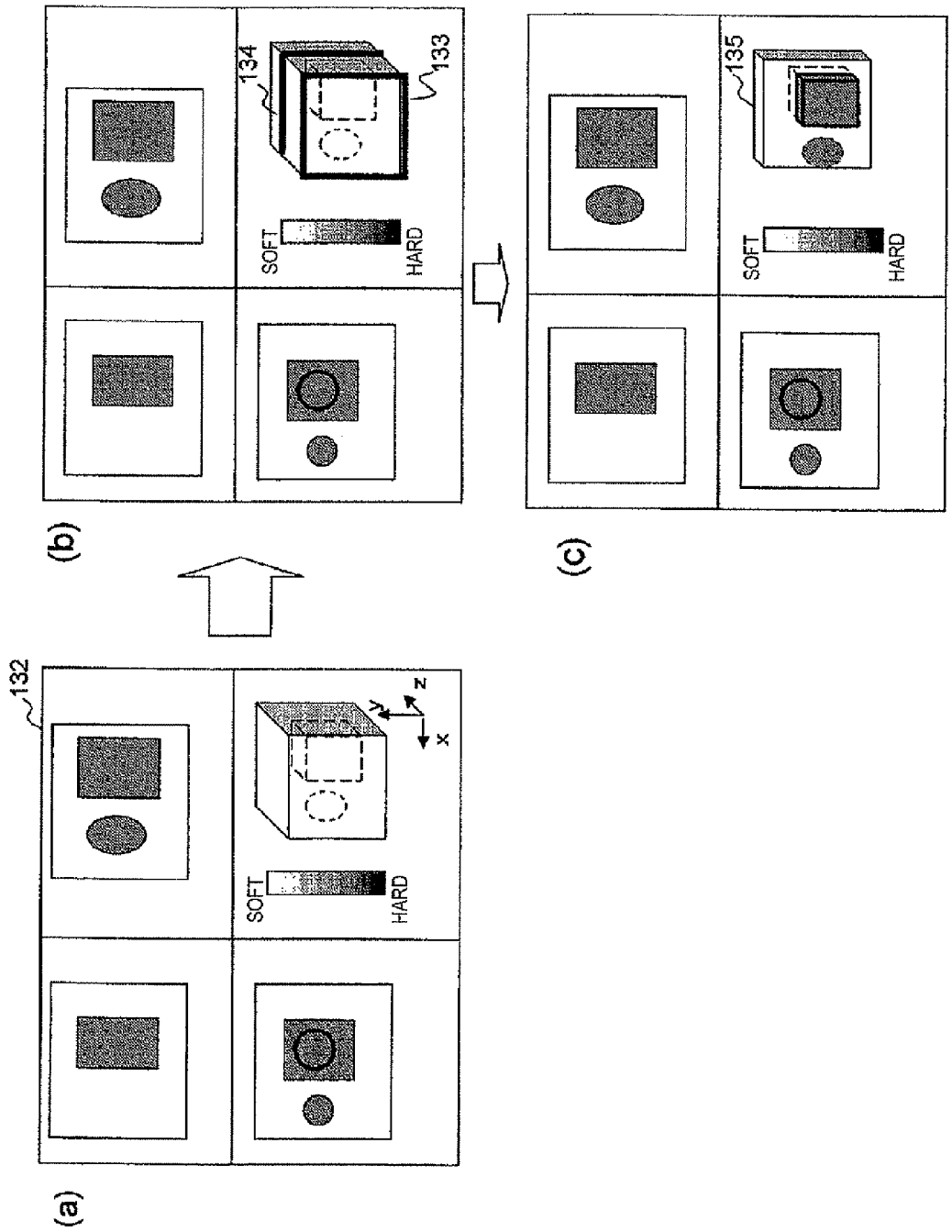
FIG. 10 is a view for explaining an image display example generated by the construction of a 3-dimensional elastic image in the seventh embodiment illustrated in FIG. 9.

FIGS. 9 and 10 show an example of display images in the seventh embodiment. As shown in FIG. 9(a), an extracted elastic volume 130 is extracted. The selecting volume calculation unit 53, as shown in FIG. 9(b), forms and outputs a volume mask 131 in which "1" is set on the voxels where the extracted elastic volume 130 exists and "0" is set on the voxels where the extracted volume does not exist. The elastic volume rendering unit 42 performs volume rendering including the volume which is not extracted, and displays the rendered volumes as shown in FIG. 10.

In concrete terms, the operator compresses the X-Y plane of a 3-dimensional elastic image, from a cross-sectional position 133 to a cross-sectional position 134 as shown in FIG. 10(b) via the interface unit 43. The volume rendering unit 42 sets, among the voxels included from the cross-sectional position 133 to the cross-sectional position 134 as well as in the volume mask 131, "0" on the elasticity value of the voxels having "0", and displays a volume 135 as shown in FIG. 10(c). In this manner, while the volumes in which regions of interest are set and extracted remain, it is possible to observe the relationship between the cross-sections of the extracted volumes and the surrounding volumes. The idea of the volume mask 131 in the present embodiment can also be applied to the editing with the exception of elimination. Also, the editing can be performed on the voxels corresponding to the positions having in the volume mask 131.

In other words, the present embodiment comprises the selecting volume calculation unit configured to perform masking on extracted elastic volumes and output the masked regions, and the 3-dimensional elastic image creation unit executes the volume editing process only on the masked regions.

Description of Reference Numerals 1 object
2 ultrasonic probe
3 transmission unit
4 reception unit
5 ultrasonic transmission/reception control unit
6 phasing and adding unit
7 tomographic image constructing unit
12 switching and synthesizing unit
13 image display unit
27 RF signal frame data storing unit
28 RF signal frame data selecting unit
30 displacement measuring unit
32 elasticity information calculation unit
34 elastic image constructing unit
35 2-dimensional tomographic image storing unit
36 tomographic volume data creation unit
38 tomographic volume rendering unit
39 2-dimensional elastic image storing unit
40 elastic volume data creation unit
42 elastic volume rendering unit
43 interface unit
44 image system control unit
46 tomographic multi-frame constructing unit
47 minor-axis scan position control unit
48 elastic multi-frame constructing unit
51 selecting coordinate calculation unit
52 selecting elasticity value calculation unit
53 selecting volume calculation unit

The invention claimed is:

1. An ultrasonic diagnostic apparatus including:
a storage unit configured to store elastic volume data generated based on ultrasonic image data acquired by transmitting/receiving ultrasonic waves to/from an object to be examined:
an input unit configured to set a region of interest in a space which is occupied by the elastic volume data;
an extraction unit configured to extract from the elastic volume data a voxel group having voxel values within a set elasticity range which is set based on an elasticity value of voxels in the region of interest;
a 3-dimensional elastic image creation unit configured to generate a 3-dimensional elastic image by volume rendering the elastic volume data of the voxel group which is extracted by the extraction unit or the elastic volume data excluding the extracted voxel aroup; and
an image display unit configured to display the 3-dimensional elastic image generated by the 3-dimensional elastic image creation unit,
wherein the extraction unit extracts central coordinates and the voxels that are consecutively connected to the voxel positioned at the central coordinates in the region of interest as the voxel group.

2. The ultrasonic diagnostic apparatus according to claim 1 further comprising a cross-sectional image generation unit configured to generate 3-cross-sectional elastic images of the elastic volume data in the orthogonal three cross-sections that are set by the input unit and displays the generated images on the image display unit, wherein the input unit sets and inputs the region of interest in one of the 3-cross-sectional elastic images that are displayed on the image display unit.

3. The ultrasonic diagnostic apparatus according to claim 1, further comprising a cross-sectional image generation unit configured to generate 3-cross-sectional elastic images of the elastic volume data in the orthogonal three cross-sections that are set by the input unit and displays the generated images on the image display unit, wherein the input unit sets and inputs the region of interest in any of the 3-cross-sectional elastic images that are displayed on the image display unit.

4. The ultrasonic diagnostic apparatus according to claim 2, wherein the 3-dimensional elastic image and the 3-cross-sectional elastic images are color elastic images in which the hue is converted in accordance with the elasticity value of the pixels.

5. The ultrasonic diagnostic apparatus according to claim 2, wherein the cross-sectional image generation unit generates extracted 3-cross-sectional elastic images in the orthogonal 3-cross-sections of the elastic volume data of the voxel group which is extracted in the extraction unit or the elastic volume data excluding the extracted voxel group, synthesizes the generated images with the 3-cross-sectional elastic images, and displays the synthesized image on the image display unit.

6. The ultrasonic diagnostic apparatus according to claim 2, wherein:
the input unit is configured capable of enlarging and reducing the region of interest which is set on the 3-cross-sectional elastic images displayed on the image display unit;
the extraction unit re-extracts the voxel group in the enlarged or reduced region of interest; and
the 3-dimensional elastic image creation unit generates a 3-dimensional elastic image for the re-extracted voxel group.

7. The ultrasonic diagnostic apparatus according to claim 1, wherein:
the extraction unit, when a plurality of the regions of interest are set by the input unit, extracts the voxel groups included in the respective regions of interest; and
the 3-dimensional elastic image creation unit generates a 3-dimensional elastic image by volume rendering the elastic volume data of the voxel groups which are extracted by the extraction unit or the elastic volume data excluding the extracted voxel groups, and displays the generated image on the image display unit.

8. The ultrasonic diagnostic apparatus according to claim 1, wherein:
the extraction unit, when a plurality of the regions of interest are set by the input unit, extracts the voxel groups included in the respective regions of interest; and
the 3-dimensional elastic image creation unit generates a 3-dimensional elastic image by volume rendering the elastic volume data of the voxel groups which are extracted by the extraction unit or the elastic volume data excluding the extracted voxel groups, and displays the generated image on the image display unit.

9. An ultrasonic diagnostic apparatus including:
a storage unit configured to store elastic volume data generated based on ultrasonic image data acquired by transmitting/receiving ultrasonic waves to/from an object to be examined;
an input unit configured to set a region of interest in a space which is occupied by the elastic volume data;
an extraction unit configured to extract from the elastic volume data a voxel group having voxel values within a set elasticity range which is set based on an elasticity value of voxels in the region of interest;
a 3-dimensional elastic image creation unit configured to generate a 3-dimensional elastic image by volume rendering the elastic volume data of the voxel group which is extracted by the extraction unit or the elastic volume data excluding the extracted voxel group; and
an image display unit configured to display the 3-dimensional elastic image generated by the 3-dimensional elastic image creation unit,
wherein:
the extraction unit, when a plurality of the regions of interest are set by the input unit, calculates an average value of elasticity values in a plurality of voxels included in the respective regions of interest, and extracts the voxels included in the elasticity range having an upper limit value and a lower limit value that are set based on the average value, as well as central coordinates in the respective regions of interest and the voxels that are consecutively connected to the voxel positioned at the central coordinates, as voxel groups; and
the 3-dimensional elastic image creation unit generates a 3-dimensional elastic image by volume rendering the elastic volume data of the voxel groups that are extracted by the extraction unit or the elastic volume data excluding the extracted voxel groups and causes the generated image to be displayed on the image display unit.

10. The ultrasonic diagnostic apparatus according to claim 7, wherein the 3-dimensional elastic image creation unit, at the time that the region of interest which has the smaller average value of the elasticity values in the voxels therein from among the set two regions of interest are volume rendered, generates the 3-dimensional elastic image by making the opacity small.

11. An ultrasonic diagnostic apparatus including:
a storage unit configured to store elastic volume data generated based on ultrasonic image data acquired by transmitting/receiving ultrasonic waves to/from an object to be examined;
an input unit configured to set a region of interest in a space which is occupied by the elastic volume data;
an extraction unit configured to extract from the elastic volume data a voxel group having voxel values within a set elasticity range which is set based on an elasticity value of voxels in the region of interest;
a 3-dimensional elastic image creation unit configured to generate a 3-dimensional elastic image by volume rendering the elastic volume data of the voxel group which is extracted by the extraction unit or the elastic volume data excluding the extracted voxel group;
an image display unit configured to display the 3-dimensional elastic image generated by the 3-dimensional elastic image creation unit, and
a selecting volume calculation unit configured to perform masking on extracted elastic volume data and output the masked region, wherein the 3-dimensional elastic image creation unit performs a volume editing process only on the masked region.

12. The ultrasonic diagnostic apparatus according to claim 7, wherein the 3-dimensional elastic image creation unit, at the time that the region of interest which has the larger average value in the elasticity values of the voxels therein from among the set two regions of interest is volume rendered, generates the 3-dimensional elastic image by making the opacity small.

13. The ultrasonic diagnostic apparatus according to claim 10, wherein the elasticity value is the elasticity modulus or viscosity.

14. The ultrasonic diagnostic apparatus according to claim 12, wherein the elasticity value is the strain or displacement.

* * * * *